(12) United States Patent
Hommann et al.

(10) Patent No.: US 7,361,160 B2
(45) Date of Patent: Apr. 22, 2008

(54) INJECTION APPARATUS COMPRISING A NEEDLE-PROTECTING DEVICE

(75) Inventors: Edgar Hommann, Grossaffoltern (CH); Benjamin Scherer, Uster (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 11/135,602

(22) Filed: May 23, 2005

(65) Prior Publication Data

US 2005/0273061 A1 Dec. 8, 2005

Related U.S. Application Data

(63) Continuation of application No. PCT/CH03/000757, filed on Nov. 17, 2003.

(30) Foreign Application Priority Data

Nov. 25, 2002 (CH) .................................. 1986/02

(51) Int. Cl.
  *A61M 5/32* (2006.01)
(52) U.S. Cl. ..................................... 604/198
(58) Field of Classification Search ................ 604/198, 604/162, 164.08, 192, 232
  See application file for complete search history.

(56) References Cited

U.S. PATENT DOCUMENTS

| | | | | |
|---|---|---|---|---|
| 5,114,406 A | * | 5/1992 | Gabriel et al. | 604/136 |
| 5,201,708 A | * | 4/1993 | Martin | 604/110 |
| 5,271,744 A | * | 12/1993 | Kramer et al. | 604/506 |
| 5,609,577 A | * | 3/1997 | Haber et al. | 604/110 |
| 5,658,259 A | * | 8/1997 | Pearson et al. | 604/232 |
| 5,666,966 A | * | 9/1997 | Horie et al. | 600/573 |
| 6,099,504 A | * | 8/2000 | Gross et al. | 604/140 |
| 6,171,276 B1 | * | 1/2001 | Lippe et al. | 604/67 |
| 6,939,330 B1 | * | 9/2005 | McConnell-Montalvo et al. | 604/197 |
| 6,989,001 B2 | * | 1/2006 | Chen | 604/110 |
| 7,004,929 B2 | * | 2/2006 | McWethy et al. | 604/198 |
| 7,029,461 B2 | * | 4/2006 | Ferguson et al. | 604/198 |
| 7,118,552 B2 | * | 10/2006 | Shaw et al. | 604/110 |
| 2002/0193746 A1 | * | 12/2002 | Chevallier | 604/197 |
| 2002/0193749 A1 | * | 12/2002 | Olovson | 604/198 |
| 2005/0049561 A1 | * | 3/2005 | Hommann et al. | 604/263 |
| 2005/0203466 A1 | * | 9/2005 | Hommann et al. | 604/240 |
| 2005/0273061 A1 | * | 12/2005 | Hommann et al. | 604/198 |
| 2005/0277886 A1 | * | 12/2005 | Hommann et al. | 604/136 |

FOREIGN PATENT DOCUMENTS

WO     WO 99/07425     2/1999

* cited by examiner

*Primary Examiner*—Kevin C. Sirmons
*Assistant Examiner*—Deanna K Hall
(74) *Attorney, Agent, or Firm*—David E. Bruhn; Dorsey & Whitney LLP

(57) ABSTRACT

An injection device including a receptacle for an active substance, which is connected to an injection needle and is accommodated inside a sliding sleeve that can be displaced within a housing by a driving force. A sleeve-shaped needle-protecting device is displacable within the housing by a spring such that the needle-protecting device moves forward and extends past the injection needle in an axial direction when the injection needle is withdrawn from the body tissue. A lock prevents the needle-protecting device from being manually pushed backward, the lock effective between the needle-protective device and the sliding sleeve, and being automatically deactivated when the sliding sleeve is at least approximately back in its retracted position.

12 Claims, 2 Drawing Sheets

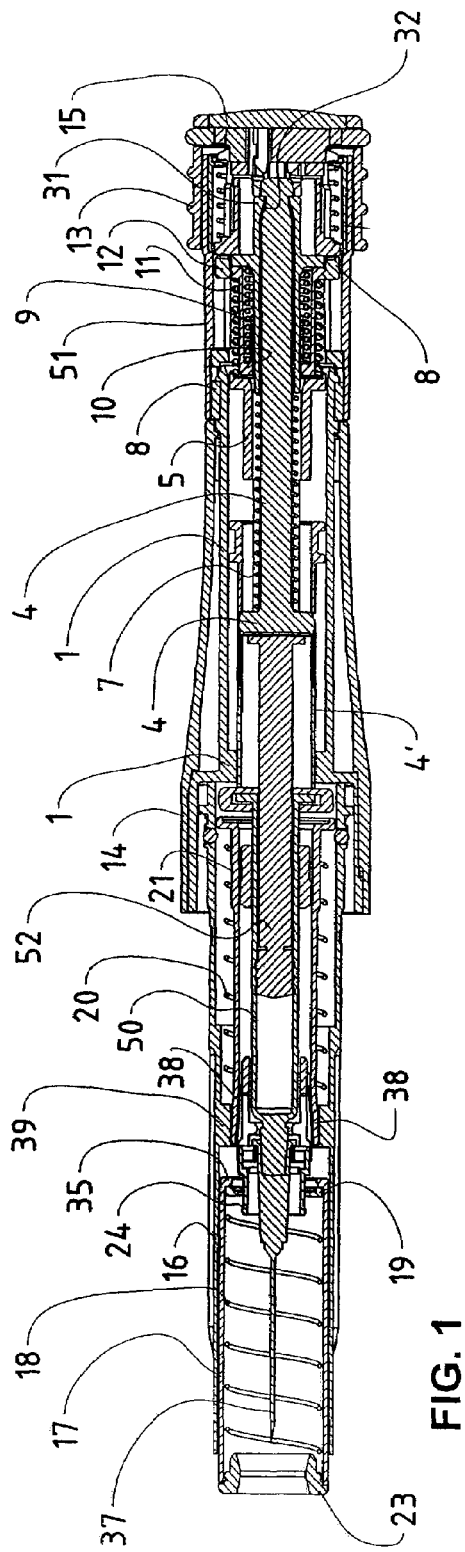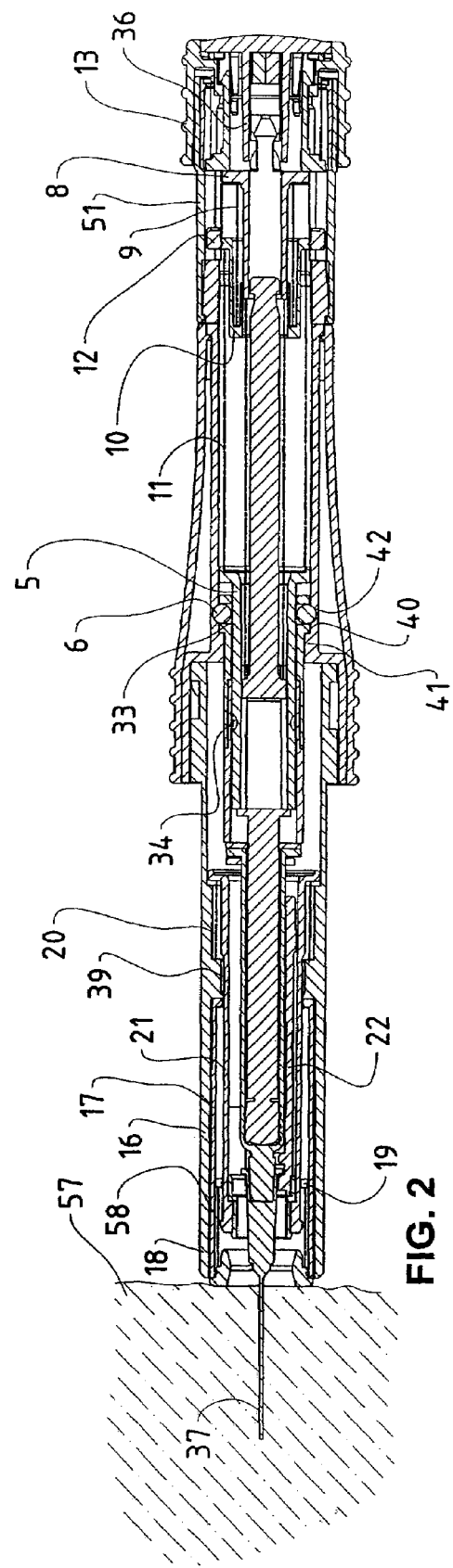

INJECTION APPARATUS COMPRISING A NEEDLE-PROTECTING DEVICE

CROSS-REFERENCE TO RELATED APPLICATION(S)

This application is a continuation of International Application No. PCT/CH2003/000757, filed on Nov. 17, 2003, which claims priority to Swiss Application No. 1986/02, filed on Nov. 25, 2002, the contents of which are incorporated in their entirety by reference herein.

BACKGROUND

The application relates to devices and methods for delivering, administering, dispensing or injection a substance. More particularly, it relates to an apparatus for injecting an active substance having an injection needle, a housing, a receptacle for the active substance, an injection piston that is displaceable in the receptacle for the purpose of expelling the active agent, and a needle protecting device that is displaceable relative to the housing.

A task of needle protecting or covering device is to protect persons from unintentional injury by an injection needle after the use of an injection apparatus. An advantage of such devices is also that the patient is spared a view of the injection needle, which is felt as unpleasant by many people. Needle protecting devices, caps or covers are known in many forms, both in connection with manually operated syringes and with so-called autoinjectors.

For example, the document WO09714455 describes an autoinjector having a needle protecting sleeve that is displaceable in a housing, including a sleeve which during the injection rests against the skin of the patient and is prestressed by a spring such that, upon retraction of the autoinjector, the needle protecting sleeve is pushed forward relative to the autoinjector and covers the injection needle. Locking means operative between the needle protecting sleeve and the housing ensure that the needle protecting sleeve cannot be pushed back again and, thus, that no unintentional injury by the injection needle can occur. Means for canceling or releasing the locking are not disclosed.

SUMMARY

In one embodiment, the present invention provides for an injection device and method wherein, during skin penetration of an injection needle associated with the device, a needle protecting device remains in an substantially constant position relative to a housing and, in the process, a spring element is stressed, which spring element, after the removal of the injection needle from the skin, pushes the needle protecting device forward into a position in which the needle is substantially covered or surrounded.

In one embodiment, the present invention comprises an injection device comprising a receptacle or container for an active substance, which is connected to an injection needle and is accommodated inside a sliding sleeve that can be displaced within a housing by means of a driving force. A sleeve-shaped needle-protecting device is displaceable within the housing by means of a spring such that said needle-protecting device moves forward and extends past the injection needle in an axial direction when the injection needle is withdrawn from the body tissue. A lock prevents the needle-protecting device from being manually pushed backward, the lock effective between the needle-protective device and the sliding sleeve, and being automatically deactivated when the sliding sleeve is at least approximately back in its retracted position.

An embodiment of the invention is characterized in that the receptacle is accommodated inside a sliding sleeve, which during the skin penetration is shifted in the housing from a retracted position into an advanced position, that the needle protecting device in its advanced position is automatically locked by locking means, which are arranged and designed such that they are operative between the needle protecting device and the sliding sleeve when the needle protecting device and the sliding sleeve are located in their advanced position, and that means for disengaging the locking means are present, which disengaging means are operative when the sliding sleeve is located at least approximately in its retracted position.

The needle protecting device is thus not, as in many known devices of this type, locked against the housing, but rather the sliding sleeve, and the means for disengaging the locking mechanism are operative only when the sliding sleeve is located at least approximately in its retracted position. This provides the advantage that the injection needle is already situated again inside the housing when the locking mechanism is disengaged. Consequently, in any operating state of the autoinjector it is ensured that the injection needle cannot be unintentionally touched.

According to a further embodiment of the invention, the locking means displays at least one flexible tongue that is arranged on the sliding sleeve and is oriented in an essentially axial manner, which flexible tongue, in its relaxed state, forms an axial stop with a region of the needle protecting device. Further, the means for disengaging the locking mechanism display an inward-jutting projection arranged in the housing, which projection in the retracted position of the sliding sleeve presses the flexible tongue in a radially-inward manner, in such a way that the part of the sliding sleeve containing the flexible tongue can slip into the region of the needle protecting device. Through these measures, an autoinjector can be realized in a simple and cost-effective manner and, moreover, has a relatively short structural length.

According to another embodiment of the invention, a spring element is present which presses the needle protecting device into its advanced position and which is stressed by the sliding sleeve when the latter moves into its advanced position. This has the advantage that the needle protecting device is not pushed in the direction of the skin of the patient until the needle is stuck in.

A further embodiment of the invention provides for the presence of carrier means that cause the needle protecting device to be carried along by the sliding sleeve when the latter is guided from its advanced position into the retracted position. It is thus no longer necessary to manually push the needle protecting device back into the housing after unlocking has taken place. If, in addition, a restoring spring is provided, which acts on the sliding sleeve with a restoring force in the direction of its retracted position, then both the sliding sleeve and the needle protecting device automatically assume the retracted starting position when the driving force ceases.

BRIEF DESCRIPTION OF THE DRAWINGS

FIG. 1 shows a longitudinal section through an exemplary embodiment of an autoinjector according to the invention, in the loaded state;

FIG. 2 shows a longitudinal section through the same autoinjector after the insertion of the injection needle and the expelling of the medication, the sectional plane being shifted by 90° with respect to that of FIG. 1;

DETAILED DESCRIPTION OF THE DRAWINGS

Figure 3:
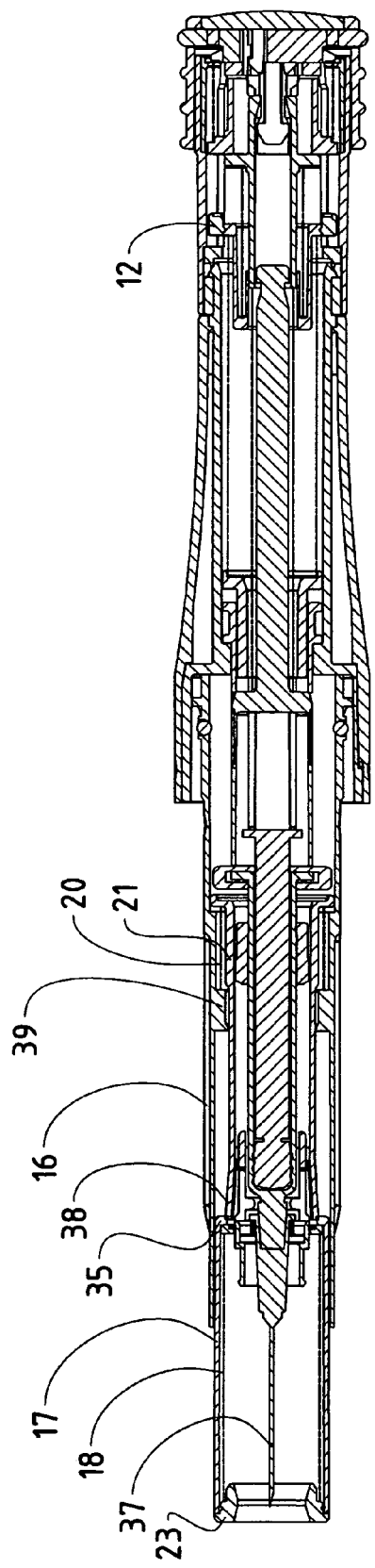
FIG. 3 shows a longitudinal section through the same autoinjector after the withdrawal of the injection needle, the sectional plane being the same as in the representation according to FIG. 1.

An autoinjector in accordance with the present invention comprises two main components, namely the reservoir part, shown on the left in the figures, which accommodates a filled syringe 50, and the power pack, shown on the right in the figures, in which are accommodated the parts serving automatic insertion and expelling of the substance to be administered. The two main components are detachably connected to each other via a bayonet-like connection between a housing 16 and a power-sleeve 1. In the following description, the side of the autoinjector at which the injection needle 37 is located is referred to as the front.

With reference to FIG. 1, which shows an operation-ready autoinjector, the power pack is first described. The parts for the propulsion of the injector are accommodated in the grip housing 14, to the rear end of which an indicator window 51 is attached. The indicator window 51 is, for example, produced from a transparent or translucent material, so that the indicator 12 displaceably held in the indicator window 51 can be observed from the outside. The indicator 12 permits the user to optically follow the process of the expelling of the medication. Arranged at the rear end of the autoinjector is the actuation knob 13, which at its rearward face side is provided with a cover disc 15. The power sleeve 1 is accommodated inside the grip sleeve 14. At its rear end, the power sleeve 1 is connected to a catch sleeve 8 by means of a snap connection. The catch sleeve 8, for its part, displaceably accommodates a spring sleeve 10 in its interior. The spring sleeve 10 is coupled at the rear to the indicator 12 through a snap connection. At the front side of the spring sleeve 10, the transfer part 5 is displaceably seated in the power sleeve 1. The transfer part 5 has the task of actuating the piston rod 52 of the syringe 50 in order to expel the contents of the syringe, as will be described below. Within the spring sleeve 10, a spring 9 is accommodated in a stressed state, which spring is supported at the front on the spring sleeve 10 and at the rear presses against the catch sleeve 8. A second spring 11, likewise in the stressed state, is located outside the spring sleeve 10 and is supported at the front against the transfer part 5 and at the rear presses against the spring sleeve 10.

A piston guide 4 is situated with its front, sleeve-shaped, slotted end 4' against the shoulder of the syringe 50 and extends through the transfer part 5, the spring sleeve 10, and the catch sleeve 8 into the region of the actuation knob 13. The piston guide 4 is prestressed forward by means of a spring 7, which is supported at the rear against the catch sleeve 8. At its rear end, the piston guide 4 is held in the position shown in FIG. 1 by two catch lobes 31 formed on the catch sleeve 8, which lobes engage a groove 32 formed on the rear end of the piston guide 4. Catch members, for example balls 6 (visible in FIG. 2), which are accommodated in radial openings 33 of the piston guide 4 and engage depressions 34 in the transfer part 5, ensure in this operating position that the transfer part 5 and the piston guide 4 can only move in common. Instead of balls 6, any suitable mechanism or body can also be used as catch members, for example pins.

The description of the reservoir part now follows. The parts for the accommodation of the syringe 50 are, as mentioned, placed in the housing 16, which is connectable to the power sleeve 1, as described. A sliding sleeve 21 accommodates in itself the syringe 50 with the interposition of a needle holder 22 (FIG. 2). The needle holder 22 ensures, in the case of luer slip couplings, that the injection needle 37 cannot be withdrawn from the syringe so long as the latter is located in the autoinjector. Toward the front, the needle holder 22 lies against a support ring 24 connected to the sliding sleeve 21. In the case of syringes and needles with luer lock couplings, in which therefore the injection needle is connected to the syringe by means of a thread, no needle holder 22 is present. The sliding sleeve 21 is displaceable within the housing 16 and is pressed by a spring 20 into the operating position showing in FIG. 1. For this purpose, the spring 20, which in the operating position according to FIG. 1 is located in its only slightly prestressed state, supports itself at the front against a circular inner step 39 of the housing 16 and at the rear against a outward-projecting brim of the sliding sleeve 21. A sleeve-shaped needle protecting device 17 is displaceable within the housing 16. The needle protecting device 17 is closed toward the front by means of a snap cover 23, which leaves open a passage for the injection needle 37 and has an inward-pointing flange 35 at its rear end. A spring 18 is supported at the front against the snap cover 23 and at the rear against an carrier ring 19, which for its part is supported, in the operating position according to FIG. 1, against the flange 35. Consequently, in the operating position according to FIG. 1, in which the spring 18 is only slightly prestressed, this spring has no effect, because its remaining prestress force is taken up by the needle protecting device 17.

Before an injection can be triggered, the autoinjector must be unlocked. For this purpose, the actuation knob 13 is moved toward the rear. In the process, at the front edge of the actuation knob 13 a region of the indicator window 51 becomes open, at the inside of which a conspicuously colored warning sleeve becomes visible, indicating clearly that the autoinjector is now unlocked and ready for the injection. With the unlocking movement, tongues 36 formed on the inside of the cover disc 15 of the actuation button 13 slide over the catch lobes 31 formed on the catch sleeve. The tongues 36 and the catch lobes 31 are here shaped such that the tongues 36 yield elastically in a radial direction while they slide over the ends of the catch lobes 31, which hold fast the piston guide 4 by engaging the mentioned grooves 32. After the unlocking movement, the tongues 36 formed on the actuation knob 13 are situated between the catch lobes 31 in the manner of wedges.

The autoinjector is now ready for the injection and is placed with the snap cover 23 at the desired location on the skin of the patient. Since the needle protecting device 17 has axial play in the housing 16, it moves toward the rear upon being placed against the skin, until the flange 35 rests against the step 39. The patient holds the autoinjector firmly at the grip sleeve 14 and moves the actuation knob 13 forward, i.e. in the direction of his or her body. In this triggering movement, the tongues 36 press between the catch lobes 31 and spread these radially away from each other, whereby the piston guide 4 is released and thrust forward through the force of the spring 7. The sticking-in motion is also assisted through the force of the springs 9 and 11, which act upon the transfer part 5. Since the transfer part 5 is connected to the piston guide 4 via the balls 6, there exists a spring system consisting of the springs 7, 9, and 11 having a relatively high starting force, which contributes to the reliable advancing of the injection needle to the full penetration depth. The force of the springs is transferred to the shoulder of the syringe 50 via the sleeve-shaped front end 4' of the piston guide 4 and pushes this shoulder, along with the sliding sleeve 21 in which it is accommodated, in a forward direction, so that the injection needle 37 is advanced and the skin of the patient penetrated. The front end of the sliding sleeve 21 moves into the needle protecting device 17, taking along with it the carrier ring 19 on its provided flexible tongues 38 and thus stressing the spring 18. With this insertion motion, the sliding sleeve 21 also compresses the spring 20. The insertion stroke is limited through the abutting of the shoulder 40 of the piston guide 4 against an inner step 41 of the power sleeve 1. In this end position, the openings 33 in the piston guide 4, which accommodate the balls 6, align with depressions 42 provided in the power sleeve 1, the balls 6 can give way radially to the outside, and the coupling between the piston guide 4 and the transfer part 5 is canceled. Simultaneously, the piston guide 4 is now locked against the power sleeve 1, so that the force of the spring 20 is absorbed by the power sleeve and does not counteract the force of the spring 7. The injection now begins automatically, as the piston rod 52 of the syringe 50 is further thrust forward by the transfer part 5 under the force of the springs 11 and 9 and thereby the medication contained in the syringe 50 is expelled. FIG. 2 shows the just-described operating state of the autoinjector, in which the medication has been completely expelled, as can be seen in the figure through the position of the piston rod of the syringe 50. The user can clearly recognize this operating state by the position of the indicator 12 in the indicator window 51. Labeled with reference numeral 57 is the body tissue of the patient, in which the injection needle 37 remains.

Starting from the operating position represented in FIG. 2, the user can now retract the autoinjector, which then changes over to the operating position represented in FIG. 3. The spring 18, which, as described, was prestressed during the insertion process, ensures that the needle protecting device 17 remains in contact with the skin of the patient during the retraction of the autoinjector. Thus, during the withdrawal of the injection needle 37 the needle protecting device 17 shifts forward relative to the housing and to the sliding sleeve 21, until it completely covers the injection needle 37. The flexible tongues 38 snap outward behind the flange 35 of the needle protecting device 17 and prevent the needle protecting device 17 from being pushed back into the housing 16, as can be clearly seen in FIG. 3. Through this means, any further, undesired stick injury by the injection needle is eliminated. Small hooks 58 (FIG. 2), which are formed on the sliding sleeve 21 at the front and against which the flange 35 of the needle protecting device 35 rests, prevent the needle protecting device 17 from falling out of the housing 16 toward the front. If one attempts to push the needle protecting device 17 back into the housing 16, for example through pressure on the snap cover 23, this is prevented through the fact that the pressure is passed via the flexible tongues 38 to the sliding sleeve 21, from this to the syringe 50, and from this to the piston guide 4. The latter is, as mentioned, locked to the power sleeve 1 by the balls 6, so that the needle protecting device 17 cannot be pushed back into the housing 16 even with considerable expenditure of force. As a result, persons who handle the autoinjector are reliably protected from being unintentionally injured again by the injection needle 37 after a successful injection.

Figure 4:
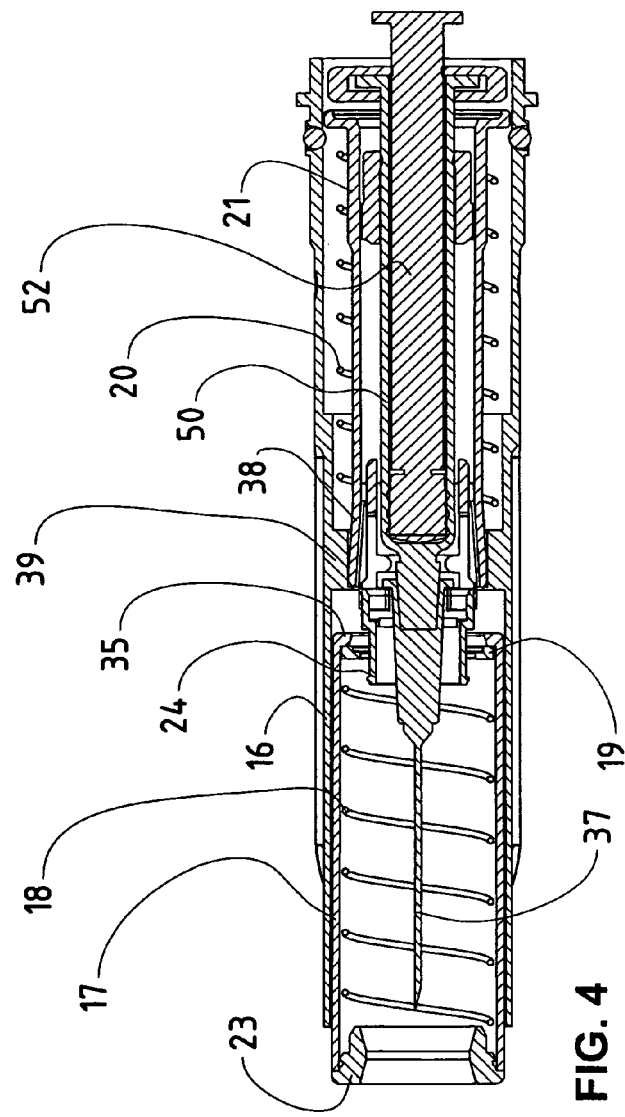
FIG. 4 shows a longitudinal section through the front part of the autoinjector after the syringe has reverted to the starting position and is ready for removal, the sectional plane being the same as in the representation according to FIG. 1.

In order to prepare the autoinjector for another use, the housing 16 and the power sleeve 1 are separated from each other through disconnection of the bayonet-type connection. Through this, both the force exerted on the piston rod 52 of the syringe 50 by the springs 9 and 11 via the transfer part 5 and the force exerted on the shoulder of the syringe 50 by the spring 7 via the piston guide 4 are eliminated, so that now the spring 20, having been stressed during the insertion, pushes the sliding sleeve 21, relative to the housing 16, back to its rearward end position. In the process, the sliding sleeve 21, via its hooks 58, also carries along the needle protecting device 17. FIG. 4 shows the reservoir part in this operating position, in which the spent syringe 50 can now be removed and replaced with a new one.

While exemplary embodiments, including preferred embodiments, of the present invention have been described herein, it is contemplated that various modifications could be made without deviating from the spirit of the present invention. Accordingly, it is intended that the scope of the present invention be dictated by the appended claims.

The invention claimed is:

1. A device for injecting an active substance, comprising an injection needle, a housing, a receptacle for the active substance accommodated in a sliding sleeve slidable relative to the housing, a syringe piston displaceable in the receptacle for expelling the active substance, and a needle protecting device displaceable relative to the housing, wherein, during a skin penetration of the injection needle, the needle protecting device remains in a substantially constant position relative to the housing and in the process a spring element is stressed, wherein, after the removal of the injection needle from the skin, the spring element pushes the needle protecting device into an advanced position in which the needle is covered and the needle protecting device is prevented from retracting by a distal end of the sliding sleeve blocking the needle protecting device from axially moving in the direction of the housing;

wherein during the skin penetration, the sliding sleeve is displaced within the housing from a retracted position to an advanced position and the needle protecting device is automatically locked in the advanced position by a locking means operative between the needle protecting device and the sliding sleeve when the needle protecting device and the sliding sleeve are located in their advanced position; and wherein the locking means comprises at least one flexible tongue arranged on the sliding sleeve and oriented in a generally axial manner, which tongue in its relaxed state forms an axial stop with a region of the needle protecting device.

2. The device according to claim 1, further comprising means for releasing the locking means which means for releasing is operative when the sliding sleeve is located at least approximately in its retracted position.

3. The device according to claim 2, wherein the means for releasing the locking means comprises a step arranged in the housing and jutting inward, which step in the retracted position of the sliding sleeve presses the flexible tongue radially inward in such a way that part of the sliding sleeve containing the flexible tongue can move into the region of the needle protecting device.

4. The device according to claim 1, wherein the spring element presses the needle protecting device into its advanced position and is stressed by the sliding sleeve when the latter moves into its advanced position.

5. The device according to claim 1, further comprising carrier projections to cause the needle protecting device to be carried along by the sliding sleeve when the sliding sleeve is guided from its advanced position into its retracted position.

6. The device according to claim 5, further comprising a restoring spring element which acts on the sliding sleeve in the direction of the retracted position of the sliding sleeve.

7. A device for injecting an active substance comprising:
an injection needle;
a housing;
a receptacle for the active substance accommodated substantially in a moveable sleeve which is moveable relative to the housing; and
a needle protector moveable relative to the housing, wherein, during an injection, the needle protector remains in a substantially constant position relative to the housing and in the process a spring element is stressed, and wherein, after the injection, the spring element urges the needle protector into an advanced position in which the needle is covered and the needle protector is prevented from moving from the advanced position by the moveable sleeve;
wherein during an injection, the moveable sleeve is moved within the housing from a retracted position to an advanced position and the needle protector is automatically locked in the advanced position by a lock operative between the needle protector and the moveable sleeve when the needle protector and the moveable sleeve are located in their advanced position; and
wherein the lock comprises at least one flexible tongue on the moveable sleeve, said tongue oriented generally axially and having a relaxed state in which it forms an axial stop cooperative with the needle protector.

8. The device according to claim 7, further comprising a release for the lock, said release operable when the moveable sleeve is located at least approximately in the retracted position.

9. The device according to claim 8, wherein the release comprises a step associated with the housing and jutting inward, wherein, when the moveable sleeve is in the retracted position, the step presses the tongue radially inwardly such the moveable sleeve can move relative to the needle protector.

10. The device according to claim 7, wherein the spring element presses the needle protector into its advanced position and is stressed by the moveable sleeve when the moveable sleeve moves into its advanced position.

11. The device according to claim 7, further comprising carriers operably coupling the needle protector and the moveable sleeve and causing the needle protector to be moved by the moveable sleeve when the moveable sleeve moves from its advanced position to its retracted position.

12. The device according to claim 11, further comprising a restoring spring acting on the moveable sleeve in the direction of the retracted position of the moveable sleeve.

* * * * *